United States Patent [19]
Kato et al.

[11] Patent Number: 6,103,508
[45] Date of Patent: Aug. 15, 2000

[54] METHOD FOR REMOVING FUMARASE ACTIVITY, MICROORGANISMS OBTAINABLE BY THE METHOD, AND PRODUCTION OF OPTICALLY ACTIVE AMINOPOLYCARBOXYLIC ACIDS USING THE MICROORGANISMS

[75] Inventors: Mami Kato; Makoto Kaneko; Takakazu Endo, all of Kanagawa, Japan

[73] Assignee: Mitsubishi Rayon Co., Ltd., Tokyo, Japan

[21] Appl. No.: 09/179,966

[22] Filed: Oct. 28, 1998

[30] Foreign Application Priority Data

Oct. 28, 1997 [JP] Japan ................... 9-311046

[51] Int. Cl.7 ................ C12P 13/00; C12N 9/04
[52] U.S. Cl. .................. 435/184; 435/106; 435/116; 435/822; 435/830; 435/848; 435/874; 435/800; 435/820; 435/109; 435/128
[58] Field of Search .................. 435/128, 106, 435/116, 822, 830, 848, 874, 800, 820, 109, 184

[56] References Cited

U.S. PATENT DOCUMENTS 5,116,743  5/1992  Goto et al. ................. 435/116

FOREIGN PATENT DOCUMENTS

| 0731171A2 | 9/1996 | European Pat. Off. ............ 435/106 |
| 0805211 A2 | 11/1997 | European Pat. Off. . |
| 0845536 A2 | 6/1998 | European Pat. Off. . |
| 60-126092 | 7/1985 | Japan . |

OTHER PUBLICATIONS

Guest et al., Journal of Bacteriology, Feb. 1983, pp. 588–596.

Witschel et al., Biodegradation, vol. 8, No. 6, pp. 419–428, (1998).

*Primary Examiner*—Rebecca E. Prouty
*Assistant Examiner*—Richard Hutson
*Attorney, Agent, or Firm*—Birch, Stewart, Kolasch & Birch, LLP

[57] ABSTRACT

This invention relates to a method for removing fumarase activity from a microorganism or processed product thereof having ethylenediamine-N,N'-disuccinic acid ethylenediamine lyase activity, which includes treating the microorganism or processed product thereof with an aqueous alkaline solution at a pH of 8.0 to 10.5 in the presence of at least one salt with a concentration of 5 mM to 1000 mM. The salt is preferably selected from the group consisting of sodium, potassium, ammonium and $C_{2-6}$ alkanediamine salts of boric acid, phosphoric acid, hydrochloric acid, sulfuric acid, acetic acid, oxalic acid, fumaric acid, maleic acid and ethylenediamine-N,N'-disuccinic acid, and mixtures thereof. This invention also relates to a microorganism or processed product thereof having reduced fumarase activity obtainable by the above described method, and to a method for producing an optically active aminopolycarboxylic acid from fumaric acid and a compound having amino group in the presence of the microorganim or processed product thereof having reduced fumarase activity as a catalyst.

11 Claims, 6 Drawing Sheets

SEQUENCE LISTING

<160> NUMBER OF SEQ ID NOS: 6

<210> SEQ ID NO 1
<211> LENGTH: 495
<212> TYPE: PRT
<213> ORGANISM: Brevundimonas sp.
<220> FEATURE:
<223> OTHER INFORMATION: Xaa represents Met or deletion

<400> SEQUENCE: 1

```
Xaa Thr Pro His Asn Pro Asp Ala Thr Arg Ile Gly Arg Ala Lys Arg
 1               5                  10                  15

Ala Lys Ala Pro Glu Phe Gln Glu Leu Tyr Asp Phe Glu Ala Ala Ala
            20                  25                  30

Leu Thr Leu Thr Ser Ala Val Phe Pro Tyr Asp Ser Lys Ile His Arg
        35                  40                  45

Ala His Val Val Met Leu Ala Glu Gln Asp Ile Leu Thr Arg Asp Glu
    50                  55                  60

Ala Ala Ser Ile Leu Asn Gly Leu Ala Lys Ala Asp Glu Leu Ala Gly
65                  70                  75                  80

Lys Asp Ala Ala Leu Arg Thr Tyr Leu Pro Tyr Glu Ala Ala Leu Lys
                85                  90                  95

Arg Glu Ile Gly Ser Val Ala Gly Lys Met His Ile Gly Arg Ser Ala
            100                 105                 110

Asn Asp Leu Arg Asn Arg Val Asn Ala Cys Ser Cys Val Thr Ala Leu
        115                 120                 125

Arg Thr Val Glu Ala Val Ile Ala Leu Arg Glu Ala Val Val Thr Lys
    130                 135                 140

Ala Ala Asp His Leu Asp Thr Val Met Val Tyr Thr Gln Arg Lys
145                 150                 155                 160

Glu Ala Gln Pro Ile Thr Leu Gly His Tyr Leu Met Ala Ile Ser Glu
                165                 170                 175

Asn Leu Gly Lys Asn Leu Ala Arg Tyr Arg Glu Leu His Pro Arg Ile
            180                 185                 190

Asn Gln Cys Pro Leu Gly Ala Ala Thr Ala Gly Thr Gly Trp Pro
        195                 200                 205

Leu Asp Arg Asp Arg Thr Ala Ala Leu Leu Gly Phe His Gly Leu Val
    210                 215                 220

Val Asn Ser Ile Glu Gly Val Ala Gly Trp Asp His Val Ala Glu Phe
225                 230                 235                 240

Ala Phe Asp Asn Ala Val Phe Leu Ser Gly Leu Ser Arg Leu Ala Ser
                245                 250                 255

Glu Ile Gln Leu Trp Ser Thr Asp Glu Tyr Gln Met Ala Glu Leu Asp
            260                 265                 270

Ser Ala Phe Ala Gly Thr Ser Ser Ile Met Pro Gln Lys Lys Asn Pro
        275                 280                 285

Asp Ser Leu Glu Arg Ser Arg Lys Gly Ala Phe Ala Met Gly Pro
    290                 295                 300

Leu Val Ala Ile Leu Thr Ser Leu Asn Gly Ile Glu Tyr Gln Tyr Ser
305                 310                 315                 320

Ala Ala Arg Val Glu Leu Glu Pro Arg Ser Ile Asp Ala Leu Ile Ala
                325                 330                 335

Ala Thr His Ala Met Thr Gly Val Val Arg Thr Leu His Pro Asn Lys
            340                 345                 350
```

```
Glu Gln Asp Ala Cys Ala Met Arg Gln Glu Asn Tyr Ala Thr Met Thr
            355                 360                 365

Asp Leu Thr Asp Leu Leu Val Arg Arg Ile Gly Ile Asp Tyr Arg Glu
        370                 375                 380

Ala His Glu Ile Val Ala Arg Val Val Met Thr Ala Ile Glu Arg Gly
385                 390                 395                 400

Ile Lys Ala Asn Ala Ile Gly Leu Asp Leu Val Gln Glu Ala Ala Val
                405                 410                 415

Ala Gln Thr Gly Asn Arg Ile Gly Ile Gly Ala Ala Asp Ile Ala Asp
            420                 425                 430

Ala Leu Asp Pro Val Gln Asn Val Ala Arg Arg Lys Gly Arg Gly Met
        435                 440                 445

Pro Ala Pro Glu Ser Val Arg Ala Ala Ile Ala Glu Ala Arg Gln Glu
    450                 455                 460

Leu Asp Ala Asp Lys Ala Trp Leu Glu Asp Arg Arg Ala Gly Leu Ala
465                 470                 475                 480

Asp Ala Asp Ala Ala Leu Glu Glu Ala Val Ala Gly Ile Thr Thr
                485                 490                 495
```

<210> SEQ ID NO 2
<211> LENGTH: 1922
<212> TYPE: DNA
<213> ORGANISM: Brevundimonas sp.
<220> FEATURE:
<221> NAME/KEY: mat_peptide
<222> LOCATION: (176)..(1660)

<400> SEQUENCE: 2

```
ggatcctcat cagcgagcgc tttccgtccg gcacccgtat tctgctggaa gtcctgcaca      60
gcaaccccaa tggccgcacc ttctgggagc ggatggggtt cgaccgctac gcgctctatc     120
tcgagcggcg cgccggcccc ctcacctgac cctcagacga ctagagaaga acgcgatgac     180
cccgcataac ccagatgcca cccgtatcgg ccgtgccaag cgcgcgaagg cgccggaatt     240
ccaggaactc tatgacttcg aagcagcggc actcaccctg acgagcgccg tctttcctta     300
cgacagcaag attcatcgtg ctcacgtcgt catgctggct gaacaggaca tcctgacccg     360
ggacgaggct gccagcatcc tgaacgggct ggccaaggcg gatgaactgg cgggaaagga     420
cgcggcgctg cgcacctacc tgccctatga ggccgcgctg aaacgcgaga tcggctccgt     480
tgccgggaag atgcatatcg ggcgcagtgc caacgacctc cgcaatcggg taaacgcatg     540
ttcctgcgtg acagctctgc gcaccgtcga ggctgtgatc gcattgcgcg aggcagtcgt     600
gaccaaggcc gccgaccatc tcgacacggt gatggtcgtc tacacccagc gcaaggaggc     660
ccagccgatc acgctcggcc attacctaat ggcgatcagc gaaatctggg caagaacct      720 cgcccgctat cgcgagctcc atccgcgcat caaccaatgt cccctcggcg ccgctgccac     780
ggcgggcacg ggctggccgc tggatcgcga ccgcaccgca gcactgctgg gtttccacgg     840
gctcgtcgtc aacagcatcg agggcgtggc cggctgggac cacgtcgcgg aattcgcctt     900
cgacaatgcc gtcttcctga gcggcctcag ccgcctggct tccgagatcc agctctggag     960
cacggacgag tatcagatgg cggaactcga ctccgccttc gccggcacca gcagcatcat    1020
gccgcagaag aaaaacccgg attcgctgga gcgcagccgg aaaggcgcct tcgcggcgat    1080
ggggccgctg gtcgccatcc tcacctctct caatggtatc gagtaccagt acagcgccgc    1140
cagggtcgag ctcgaaccgc gatccatcga tgcgctgatc gcggccaccc acgcgatgac    1200
```

-continued

```
gggcgtcgtg cggacgcttc atcccaacaa ggagcaagat gcttgcgcta tgcggcaaga    1260
gaactacgcc accatgaccg acctgaccga cctgctcgtc cgtcgcatcg gcatcgacta    1320
tcgcgaggcc catgagatcg tggcgcgcgt ggtgatgacg gcgatcgagc gcggcatcaa    1380
ggccaacgcc atcggactgg acctcgtgca ggaggccgcg gtcgcgcaga cgggcaaccg    1440
gatcgagatc ggtgcggccg acatcgccga tgcgctcgat ccggttcaga acgtcgcccg    1500
tcgcaagggc aggggcatgc ccgcgcccga atccgtcagg gccgccatcg cggaggcgcg    1560
tcaggaattg gacgccgaca aggcctggct agaggaccgg cgcgccgggc tggccgatgc    1620
ggatgcggcg ctggaggagg cggtggccgg catcacgacc tgaggcctgc tgcctccctg    1680
ccgaaaatct cgactcgtgg ttcaaaaaag aggggatagc catgacgaag acggtttttt    1740
tctatctgct gacgatgact gccggcgcca tgagcggctt gaccggagcg gcgcatggcc    1800
aagccatcac cgttcccgcc gcgctgaagg aaaaaggcga gttgcgtgtc ggcgtcaaat    1860
gcgacacgcc gcctgccggt ttcctcgacg aaaagggtaa gcccaccggc atcgatatcg    1920
at                                                                    1922
```

<210> SEQ ID NO 3
<211> LENGTH: 1488
<212> TYPE: DNA
<213> ORGANISM: Brevundimonas sp.

<400> SEQUENCE: 3

```
atgacccccgc ataacccaga tgccacccgt atcggccgtg ccaagcgcgc gaaggcgccg      60
gaattccagg aactctatga cttcgaagca gcggcactca ccctgacgag cgccgtcttt     120
ccttacgaca gcaagattca tcgtgctcac gtcgtcatgc tggctgaaca ggacatcctg     180
acccgggacg aggctgccag catcctgaac gggctggcca aggcggatga actggcggga     240
aaggacgcgc gcctgcgcac ctacctgccc tatgaggccg cgctgaaacg cgagatcggc     300
tccgttgccg ggaagatgca tatcgggcgc agtgccaacg acctccgcaa tcgggtaaac     360
gcatgttcct gcgtgacagc tctgcgcacc gtcgaggctg tgatcgcatt gcgcgaggca     420
gtcgtgacca aggccgccga ccatctcgac acggtgatgg tcgtctacac ccagcgcaag     480
gaggcccagc cgatcacgct cggccattac ctaatgcgca tcagcgaaaa tctgggcaag     540
aacctcgccc gctatcgcga gctccatccg cgcatcaacc aatgtcccct cggcgccgct     600
gccacgcgcg gcacgggctg gccgctggat cgcgaccgca ccgcagcact gctgggtttc     660
cacgggctcg tcgtcaacag catcgagggc gtggccggct gggaccacgt cgcggaattc     720
gccttcgaca tgccgtcttt cctgagcggc tcagccgcc tggcttccga gatccagctc      780
tggagcacgg acgagtatca gatggcggaa ctcgactccg ccttcgccgg caccagcagc     840
atcatgccgc agaagaaaaa cccggattcg ctggagcgca gccggaaagg cgccttcgcg     900
gcgatggggc cgctggtcgc catcctcacc tctctcaatg gtatcgagta ccagtacagc     960
gccgccaggt cgagctcga accgcgatcc atcgatgcgc tgatcgcggc cacccacgcg     1020
atgacgggcg tcgtgcggac gcttcatccc aacaaggagc aagatgcttg cgctatgcgg    1080
caagagaact acgccaccat gaccgacctg accgacctgc tcgtccgtcg catcggcatc    1140
gactatcgcg aggcccatga gatcgtggcg cgcgtggtga tgacggcgat cgagcgcggc    1200
atcaaggcca acgccatcgg actggacctc gtgcaggagg ccgcggtcgc gcagacgggc    1260
aaccggatcg agatcggtgc ggccgacatc gccgatgcgc tcgatccggt tcagaacgtc    1320
gcccgtcgca agggcagggg catgcccgcg cccgaatccg tcagggccgc catcgcggag    1380
```

```
gcgcgtcagg aattggacgc cgacaaggcc tggctagagg accggcgcgc cgggctggcc    1440
gatgcggatg cggcgctgga ggaggcggtg gccggcatca cgacctga               1488
```

<210> SEQ ID NO 4
<211> LENGTH: 8
<212> TYPE: PRT
<213> ORGANISM: Brevundimonas sp.
<220> FEATURE:
<221> NAME/KEY: PEPTIDE
<222> LOCATION: (1)..(8)
<223> OTHER INFORMATION: Xaa represents Met or deletion

<400> SEQUENCE: 4

```
Xaa Thr Pro His Asn Pro Asp Ala
  1               5
```

<210> SEQ ID NO 5
<211> LENGTH: 20
<212> TYPE: PRT
<213> ORGANISM: Brevundimonas sp.
<220> FEATURE:
<221> NAME/KEY: PEPTIDE
<222> LOCATION: (1)..(20)
<223> OTHER INFORMATION: Xaa represents an unidentified amino acid
       residue

<400> SEQUENCE: 5

```
Glu Ile Gly Ser Val Gly Lys Met Glu Ile Gly Arg Xaa Ala Asn Asp
  1               5                  10                  15

Leu Arg Asn Arg
            20
```

<210> SEQ ID NO 6
<211> LENGTH: 22
<212> TYPE: PRT
<213> ORGANISM: Brevundimonas sp.
<220> FEATURE:
<221> NAME/KEY: PEPTIDE
<222> LOCATION: (1)..(22)
<223> OTHER INFORMATION: Xaa represents   unidentified amino acid
       residues

<400> SEQUENCE: 6

```
Ala Ser Gly Ala Lys Ala Pro Glu Phe Gln Glu Leu Tyr Asp Phe Glu
  1               5                  10                  15

Ala Ala Xaa Leu Xaa Leu
            20
```

METHOD FOR REMOVING FUMARASE ACTIVITY, MICROORGANISMS OBTAINABLE BY THE METHOD, AND PRODUCTION OF OPTICALLY ACTIVE AMINOPOLYCARBOXYLIC ACIDS USING THE MICROORGANISMS

FIELD OF THE INVENTION

The present invention relates to a method for removing fumarase activity from a microorganism having activity for ethylenediamine-N,N'-disuccinic acid ethylenediamine lyase; to a microorganism or processed product thereof having reduced fumarase activity obtainable by the method; and a method for producing an optically active aminopolycarboxylic acid from fumaric acid and a compound having amino group in the presence of the microorganism or processed product having reduced fumarase activity.

BACKGROUND OF THE INVENTION

Ethylenediamine-N,N'-disuccinic acid ethylenediamine lyase is used as a catalyst for producing an optically active aminopolycarboxylic acid from fumaric acid and a compound having amino group. The thus-produced optically active aminopolycarboxylic acid has a specific property of capturing metal ions such as heavy metal ions. Moreover, the optically active aminopolycarboxylic acid is susceptible to biodegradation thus being expected of its use as, for example, a chelating agent, a builder for detergents and a bleaching agent for photographs.

The present inventors have previously found a novel microbial lyase activity that converts fumaric acid and ethylenediamine into S,S-ethylenediamine-N,N'-disuccinic acid (hereinafter, referred to as ethylenediamine-N,N'-disuccinic acid ethylenediamine lyase and abbreviated as EDDSase), and proposed a method for producing optically active aminopolycarboxylic acids efficiently from fumaric acid and different amines while utilizing the above-described catalytic action (see JP-A-9-140390 or U.S. Pat. No. 5,707,836). However, microorganisms possessing such EDDSase have fumarase too, which fumarase is widely present in the biological world and can hydrate most of the fumaric acid, i.e., a common substrate for EDDSase and fumarase, into malic acid. Unless the fumarase activity is removed from the microorganisms, it is difficult to obtain an optically active aminopolycarboxylic acid of interest in a satisfactory yield.

Examples of known methods for removing the fumarase activity are: a method in which a microorganism with aspartase activity is subjected to acid-treatment (see JP-B-3-55103); and a method in which a microorganism belonging to the genus Brevibacterium with aspartase activity is treated under alkaline conditions in the presence of L-aspartic acid and an ammonium ion (see JP-B-4-80678).

However, it was experimentally confirmed that the former method could not be applied to microorganisms with EDDSase activity since the loss of the EDDSase activity was greater than the loss of the fumarase activity during the treatment. The latter method is advantageous when employed for the production of L-aspartic acid wherein the microorganism to be treated is applied to the reaction system containing a large amount of L-aspartic acid, but the method was unfavorable in operability and economics for use in other reactions.

Since the EDDSase according to the present invention is an enzyme different from the above-described aspartase, it was unknown as to how to selectively remove the fumarase activity alone without loss of the EDDSase activity.

SUMMARY OF THE INVENTION

The present invention provides a method for removing fumarase activity from a microorganism or processed product thereof having ethylenediamine-N,N'-disuccinic acid ethylenediamine lyase activity, which comprises treating the microorganism or processed product thereof with an aqueous alkaline solution at a pH of 8.0 to 10.5 in the presence of at least one salt with a concentration of 5 mM to 1000 mM.

Preferred salts are selected from the group consisting of sodium, potassium, ammonium and amine salts of boric acid, phosphoric acid, hydrochloric acid, sulfuric acid, acetic acid, oxalic acid, fumaric acid, maleic acid and ethylenediamine-N,N'-disuccinic acid, and mixtures thereof.

According to the present invention, it is possible to selectively remove fumarase activity alone from a microorganism with EDDSase and fumarase activities or processed product thereof without loss of the EDDSase activity.

The present invention also provides a microorganism or processed product thereof having EDDSase activity, containing no fumarase activity. Such a microorganism is obtainable by the above-described method.

The present invention further provides a method for producing an optically active aminopolycarboxylic acid, which comprises reacting fumaric acid with a compound having amino group in the presence of the microorganism or processed product thereof having EDDSase activity, containing reduced fumarase activity; and isolating the optically active aminopolycarboxylic acid.

The term "reduced" means that the fumarase activity is decreased or does not substantially contain.

The present invention still further provides use of the microorganism or processed product thereof in a production of an optically active aminopolycarboxylic acid from fumaric acid and a compound having amino group.

This and other advantages of the present invention will become apparent to those skilled in the art upon reading and understanding the following detailed description with reference to the accompanying figures.

DESCRIPTION OF THE PREFERRED EMBODIMENTS

Figure 1:
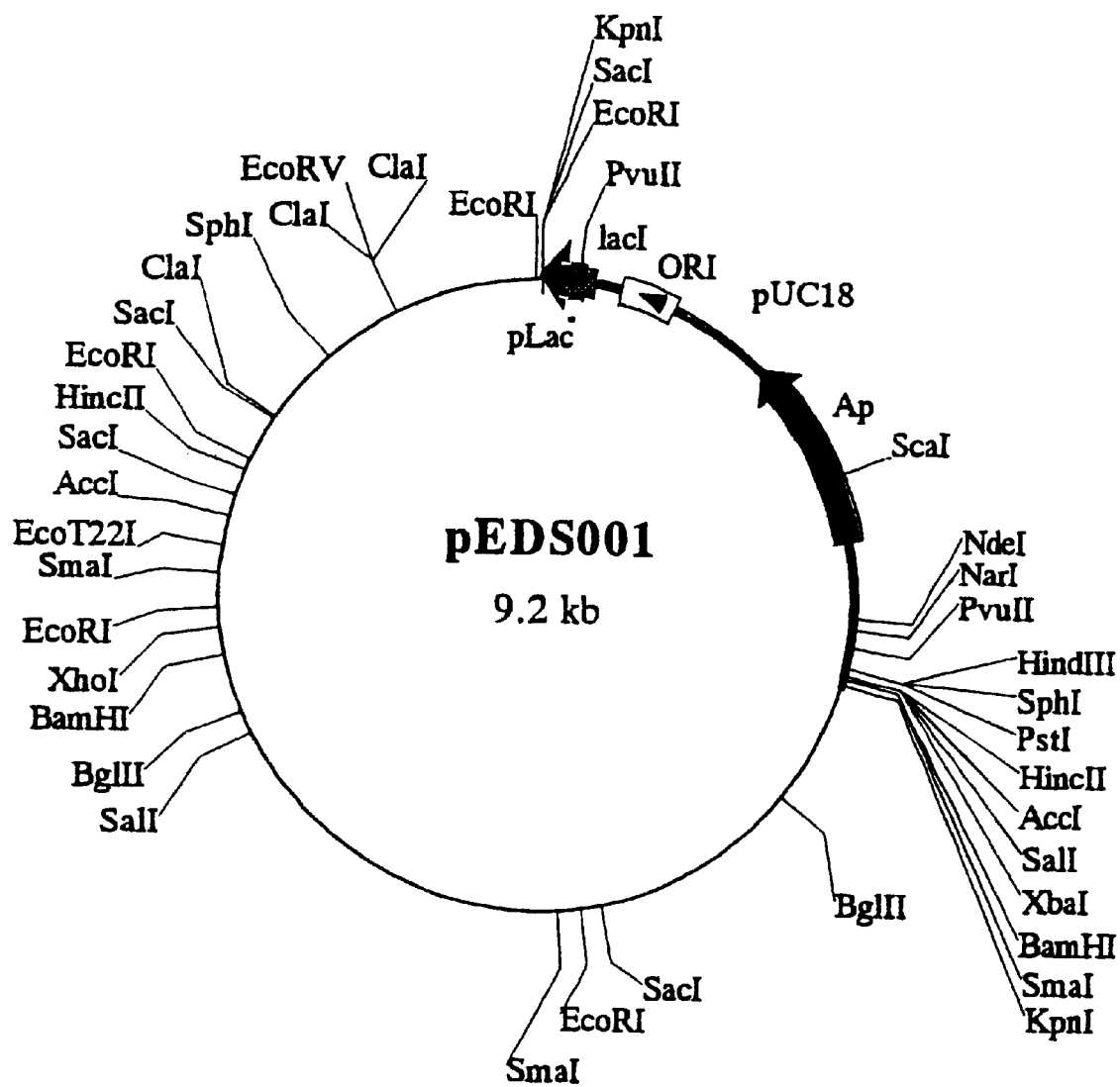
FIG. 1 is a restriction map of the plasmid pEDS001.

Through intensive studies, the present inventors have now found that the fumarase activity could be removed selectively from a microorganism or processed product thereof having EDDSase activity without loss of the EDDSase activity by treating the microorganism or processed product thereof with an aqueous alkaline solution in the presence of at least one salt.

The present invention aims at obtaining a microbial catalyst in which the fumarase activity has selectively been removed, while retaining the EDDSase activity, in order to suppress undesirable side reactions during production of optically active aminopolycarboxylic acids.

The present invention can provide its benefit in production of any optically active aminopolycarboxylic acid as long as the microbial catalyst is employed together with fumaric acid as a raw material.

A specific example that the present invention can be applied to is to produce an optically active aminopolycarboxylic acid represented by the following general formula [1], from a mixture of fumaric acid and a compound having amino group represented by the general formula [2]:

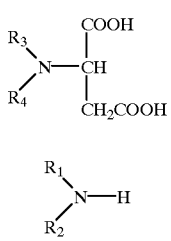

wherein $R_1$ and $R_2$, which may be identical or different, represent a hydrogen atom, a substituted or unsubstituted alkyl group, a substituted or unsubstituted cycloalkyl group, or a substituted or unsubstituted aryl group, provided that $R_1$ and $R_2$ are not hydrogen atoms at the same time; wherein the substituent is selected from the group consisting of an amino group, a cyano group, a nitro group, halogen, a hydroxyl group, a carboxyl group, an ether group and the like; and wherein $R_3$ and $R_4$ are identical to $R_1$ or $R_2$, or represent a group having the structure in which at least one amino group of $R_1$ or $R_2$ is bonded to a carbon atom of the ethylene group of succinic acid via a nitrogen atom of the amino group.

Examples of the compounds having amino group represented by the general formula [2] include alkane- and cycloalkane-diamines with a carbon number of 2 to 6 such as ethylenediamine, 1,3-propanediamine, 2-methyl-1,3-propanediamine, 2-hydroxy-1,3-propanediamine, 1,4-butanediamine, 1,5-pentanediamine, 1,6-hexanediamine, 1,2-cyclohexanediamine, 1,3-cyclohexanediamine and 1,4-cyclohexanediamine; phenylenediamines such as 1,2-phenylenediamine, 1,3-phenylenediamine and 1,4-phenylenediamine; and monoamines such as glycine, 3-aminopropionic acid, 2-aminopropionic acid, iminodiacetic acid, 3,3'-iminodipropionic acid and glutamic acid. The representative compound is ethylenediamine.

Examples of the optically active aminopolycarboxylic acid represented by the general formula [1] which can be obtained through the present invention include (S,S)-alkanediamine-N,N'-disuccinic acids, (S,S)-cycloalkanediamine-N,N'-disuccinic acids and (S,S)-phenylenediamine-N,N'-disuccinic acids, such as (S,S)-ethylenediamine-N,N'-disuccinic acid, (S,S)-1,3-propanediamine-N,N'-disuccinic acid, (S,S)-2-methyl-1,3-propanediamine-N,N'-disuccinic acid, (S,S)-2-hydroxy-1,3-propanediamine-N,N'-disuccinic acid, (S,S)-1,4-butanediamine-N,N'-disuccinic acid, (S,S)-1,5-pentanediamine-N,N'-disuccinic acid, (S,S)-1,6-hexanediamine-N,N'-disuccinic acid, (S,S)-1,2-cyclohexanediamine-N,N'-disuccinic acid, (S,S)-1,3-cyclohexanediamine-N,N'-disuccinic acid, (S,S)-1,4-cyclohexanediamine-N,N'-disuccinic acid, (S,S)-1,2-phenylenediamine disuccinic acid, (S,S)-1,3-phenylenediamine disuccinic acid and (S,S)-1,4-phenylenediamine disuccinic acid; and (S)-aspartic acid-N-monoacetic acid, (S)-aspartic acid-N-monopropionic acid, (S)-aspartic acid-N-2-propionic acid, (S)-aspartic acid-N,N'-diacetic acid, (S)-aspartic acid-N,N'-dipropionic acid and (S)-aspartic acid-N-2-glutaric acid. The typical optically active aminopolycarboxylic acid is (S,S)-ethylenediamine-N,N'-disuccinic acid.

The treatment for removing fumarase activity according to the present invention is carried out for microorganisms that will be specified later, and it is applicable to microbial cells or processed products thereof (e.g., debris of cells, cell extracts, extracted crude or purified enzymes, immobilized cells or enzymes, or cells or enzymes treated with an agent (e.g., for stabilization). The present invention may also be applied directly to microbial cells in a culture fluid following cultivation. Moreover, according to the present invention, the treatment for removing fumarase activity may optionally be followed by other treatments.

The treatment for the removal of fumarase activity can be conducted by immersing the above-described microorganisms or processed products thereof in an aqueous alkaline solution in the presence of at least one salt. The aqueous alkaline solution may contain an organic solvent such as methanol or ethanol which is freely miscible with water or other organic solvent miscible with water.

The salt usable in the present invention may be either organic or inorganic as long as it can dissolve in the aqueous alkaline solution. For example, the salt includes sodium, potassium, ammonium or amine salts of boric acid, phosphoric acid, hydrochloric acid, sulfuric acid, acetic acid, oxalic acid, fumaric acid, maleic acid and ethylenediamine-N,N'-disuccinic acid. Preferable amine is $C_{2-6}$ alkanediamines such as ethylenediamine, propanediamine, butanediamine and hexanediamine or monoamines such as triethano/amine.

The concentration of the salt is within a range of 5 mM to 1000 mM, preferably 10 mM to 500 mM. The outcome is insufficient with a concentration of less than 5 mM, and the outcome reaches the uppermost limit with a concentration of more than 1000 mM.

The aqueous alkaline solution has a pH ranging from 8 to 10.5, preferably 8.5 to 10, more preferably 9 to 9.5. The pH may be adjusted by varying the proportion of the above-mentioned acids and bases. In particular, boric acid, phosphoric acid or Good's buffer is preferably used in terms of salt concentration and pH adjustment.

According to the present invention, the treatment can be conducted at a temperature ranging from a freezing temperature to 55° C. over a period of about 1 minute to about 1 month depending on conditions. The higher the treatment temperature is set, the shorter the treatment period can be made. Alternatively, the fumarase activity may be removed during storage in a refrigerator under the above-described conditions although, in this case, the treatment period is extended.

The above-described treatment may be conducted either in a batch process or in a continuous process.

Any microorganism may be the subject of the present invention as long as the microorganism has EDDSase and fumarase activities. For example, such microorganisms include bacteria belonging to the genera Pseudomonas, Paracoccus, Sphingomonas and Brevundimonas, and transformants in which a DNA encoding EDDSase has been introduced into a host bacterium that belongs to the genus Escherichia or Rhodococcus.

Specifically, the microorganisms are Pseudomonas sp. strain TN-131 (FERM BP-5418), Paracoccus sp. strain TNO-5 (FERM BP-6547), Sphingomonas sp. strain TN-28 (FERM BP-5419), Brevundimonas sp. strain TN-30 (FERM BP-5417) and Brevundimonas Sp. strain TN-3 (FERM BP-5886), and transformants derived from the hosts *Escherichia coli* strain JM109 (ATCC53323), *Rhodococcus rhodochrous* ATCC17895 and *Rhodococcus rhodochrous* J-1 (FERM BP-1478).

Among the above-described exemplary microorganisms, the strains TN-131, TNO-5, TN-28, TN-30 and TN-3 were newly isolated from nature by the present inventors, and have been deposited with the National Institute of Bioscience and Human-Technology, Agency of Industrial Science and Technology of MITI (Ministry of International Trade and Industry) (1-3, Higashi 1-chome, Tsukuba-shi, Ibaraki-ken, 305, Japan) while being assigned with the above-identified accession numbers. Bacteriological properties of these strains are as follows.

Strain TN-131

| | |
|---|---|
| Morphology: | *bacillus* |
| Gram stain: | − |
| Spores: | − |
| Motility: | + |
| Flagellation: | polar |
| Behavior toward oxygen: | aerobic |
| Oxidase: | + |
| Catalase: | + |
| O-F test: | − |
| Color tone of colonies: | yellow |
| Production of fluorescent pigment: | + |
| Quinone system: | Q-9 |
| Nitrate reduction: | + |
| Indole production: | − |
| Glucose fermentatability: | − |
| Arginine dihydrolase: | − |
| Urea decomposition: | − |
| Esculin decomposition: | − |
| Gelatin liquefaction: | − |
| PNPG: | − |
| Utilization: | |
| glucose | − |
| L-arabinose | − |
| D-mannose | − |
| D-mannitol | − |
| N-acetyl-D-glucosamine | − |
| maltose | − |
| potassium gluconate | − |
| n-capric acid | + |
| adipic acid | − |
| dl-malic acid | + |
| citric acid | + |
| phenyl acetate | − |

Strain TNO-5

| | |
|---|---|
| Morphology: | *coccobacillus*-short rod |
| Grain stain: | − |
| Spores: | − |
| Motility: | − |
| Behavior toward oxygen: | aerobic |
| Oxidase: | + |
| Catalase: | + |
| O-F test: | − |
| Color tone of colonies: | no characteristic color generation |
| PHB accumulation: | + |
| Nitrate reduction: | − |
| Nitrite reduction: | − |
| Quinone system: | Q-10 |
| GC content of DNA (mol %) | 65 (as measured by HPLC) |

Strain TN-28

| | |
|---|---|
| Morphology: | *bacillus* |
| Gram stain: | − |
| Spores: | − |
| Motility: | + |
| Flagellation: | polar |
| Behavior toward oxygen: | aerobic |
| Oxidase: | + |
| Catalase: | + |
| O-F test: | − |
| Color tone of colonies: | yellow |
| Production of fluorescent pigment: | − |
| Quinone system: | Q-10 |
| Nitrate reduction: | − |
| Indole production: | − |
| Glucose fermentability: | − |
| Arginine dihydrolase: | − |
| Urea decomposition: | − |
| Esculin decomposition: | + |
| Gelatin liquefaction: | − |
| PNPG: | − |
| Utilization: | |
| glucose | + |
| L-arabinose | − |
| D-mannose | + |
| D-mannitol | − |
| N-acetyl-D-glucosamine | + |
| maltose | + |
| potassium gluconate | − |
| n-capric acid | − |
| adipic acid | − |
| dl-malic acid | + |
| citric acid | − |
| phenyl acetate | − |

Strains TN-30 and TN-3

| | Strain TN-30 | Strain TN-3 |
|---|---|---|
| Morphology: | *bacillus* | *bacillus* |
| Gram stain: | − | − |
| Spores: | − | − |
| Motility: | + | + |
| Flagellation: | polar | polar |
| Behavior toward oxygen: | aerobic | aerobic |
| Oxidase: | + | + |
| Catalase: | + | + |
| O-F test: | − | − |
| Color tone of colonies: | no characteristic color generated in both strains | |
| Production of fluorescent pigment: | − | − |
| PHB accumulation: | + | − |
| Requirement for Nutrition: | yes | yes |
| Quinone system: | Q-10 | Q-10 |
| Nitrate reduction: | + | + |
| Indole production: | − | − |
| Arginine dihydrolase: | − | − |
| Urea decomposition: | − | − |
| Esculin decomposition: | − | − |
| Gelatin liquefaction: | − | − |
| PNPG: | − | − |
| Utilization: | | |
| glucose | − | − |
| L-arabinose | − | − |
| D-mannose | − | − |
| D-mannitol | − | − |
| N-acetyl-D-glucosamine | − | − |
| maltose | − | − |
| potassium gluconate | + | + |
| n-capric acid | − | − |

-continued

| | | |
|---|---|---|
| adipic acid | − | − |
| dl-malic acid | − | + |
| citric acid | + | + |
| phenyl acetate | − | − |

With respect to the above-listed bacteriological properties, the strain TN-131 belongs to the genus Pseudomonas when classified according to Bergey's Manual of Systematic Bacteriology Vol. 1 (1984) and Bergey's Manual of Determinative Bacteriology 9th Ed. (1994); the strain TNO-5 to the genus Paracoccus when classified according to Bergey's Manual of Systematic Bacteriology Vol. 1 (1984); the strain TN-28 to the genus Sphingomonas when classified according to Bergey's Manual of Determinative Bacteriology 9th Ed. (1994) and Microbiol. Immunol. 34, 99 (1990); and the strains TN-30 and TN-3 both belong to the genus Brevundimonas when classified according to Bergey's Manual of Determinative Bacteriology 9th Ed. (1994) and Int. J. Syst. Bacteriol. 44, 499 (1994), respectively. In addition, the strain TN-3 has been identified as the species diminuta.

E.coli strain JM109 (ATCC53323) and Rhodococcus rhodochrous ATCC17895 are known and are available from American Type Culture Collection (ATCC). Two transformants are obtained by introducing plasmids pEDS020 and pSE001 into the above-described E.coli strain JM109 (ATCC53323) and Rhocococcus rhodochrous strain ATCC17895 as hosts, respectively, the plasmids each including a DNA encoding a protein with EDDSase activity of the strain TN-3. The thus-obtained transformants were deposited with the National Institute of Bioscience and Human-Technology, Agency of Industrial Science and Technology of MITI (Japan) as E.coli JM109/pEDS020 (FERM P-15961) on Nov. 27, 1996 which was subsequently transferred to the international deposition as FERM BP-6161 on Nov. 10, 1997; and Rhodococcus rhodochrous ATCC 17895/pSE001 (FERM P-16436) on Sep. 18, 1997 which was subsequently transferred to the international deposition as FERM BP-6548 on Oct. 15, 1998.

Hereinafter, a method for preparing the above-described transformants will be described.

(1) Preparation of Chromosomal DNA from Strain TN-3

Strain TN-3 is subjected to shake culture in 100 ml of EDDS medium (0.2% ethylenediamine-N,N'-disuccinic acid, 0.2% glucose, 0.1% bacto-yeast extract, 0.05% polypeptone, 0.28% sodium sulfate, 0.1% magnesium sulfate.7H$_2$O, 2.5%(v/v) phosphate buffer (1M, pH 7.0), and 0.5% (v/v) solution of mixed metal salts (containing 8 g of magnesium chloride.6H$_2$O, 0.8 g of calcium chloride, 0.6 g of manganese sulfate.4H$_2$O, 0.12 g of ferric chloride.6H$_2$O and 0.06 g of zinc sulfate, per 100 ml)) at 30° C. for 4 days. Then, cells are harvested and suspended in 4 ml of a saline-EDTA solution (0.1 M EDTA, 15 M NaCl, pH 8.0), followed by addition of 8 mg of lysozyme. The resultant suspension is shaken at 37° C. for 1 hour and then frozen. Ten millimeters of a Tris-SDS solution (1% SDS, 0.1 M NaCl, 0.1 M Tris, pH 9) is gently added while being shaken. Proteinase K (Merck & Co., Inc.) is further added (the final concentration: 1 mg) and the resultant is shaken at 37° C. for 1 hour. An equal volume of TE-saturated phenol (TE: 10 mM Tris, 1 mM EDTA, pH 8) is then added and stirred. After centrifugation, the supernatant is recovered to which two volumes of ethanol is added. DNA is rolled around a glass rod, and the phenol is removed therefrom by sequentially washing with 90%, 80% and 70% ethanol. The DNA is dissolved in 3 ml of TE buffer to which a ribonuclease A solution (heat-treated at 100° C. for 15 minutes) is added at the concentration of 10 mg/ml, followed by shaking at 37° C. for 30 minutes. Proteinase K is further added to the solution and the mixture is shaken at 37° C. for 30 minutes. Then, an equal volume of TE-saturated phenol is added and centrifuged to separate the mixture into upper and lower layers. The same procedure is repeated twice with the upper layer. To the resultant upper layer is added an equal volume of a chloroform solution containing 4% isoamyl alcohol, and the same extraction is repeated (hereinafter, this procedure is referred to as "phenol treatment"). Thereafter, two volumes of ethanol is added to the upper layer to recover the DNA by rolling it around a glass rod, thereby obtaining a chromosomal DNA sample.

(2) Preparation of Purified Enzyme

Strain TN-3 is subjected to shake culture in 2 L of EDDS medium at 30° C. for 4 days, harvested, suspended in 100 ml of 10 mM sodium phosphate buffer (pH 8, containing 1 mM dithiothreitol), and distrupted in a sonicator. After centrifugation at 12,000 rpm for 20 minutes, to the supernatant is added ammonium sulfate to 30% saturation, and the mixture is left at 4° C. for 30 minutes, followed by centrifugation. To the resultant supernatant, ammonium sulfate is added to give 60% saturation and left at 4° C. for 30 minutes. After centrifugation, the precipitate is dissolved in 10 ml of 10 mM sodium phosphate buffer (pH 8, containing 1 mM dithiothreitol) to prepare a solution of a partially purified enzyme.

This partially purified-enzyme solution is further purified by ion exchange chromatography. Specifically, the partially purified-enzyme solution is applied to a column (φ 10 mm×20 cm) filled with DEAE-Sephacryl (Pharmacia) equilibrated with 10 mM sodium phosphate buffer (pH 8) containing 1 mM dithiothreitol to allow adsorption. After washing the column with 40 ml of the same buffer, the enzyme is eluted with a linear gradient of 0 to 0.6 M KCl to fractionate into 2 ml fractions. Fractions exhibiting EDDSase activity are collected as a solution of the purified enzyme. When analyzed by SDS-polyacrylamide gel electrophoresis, a substantially homogeneous, single band of the enzyme is detected at the molecular weight of about 60,000 daltons.

(3) Analysis of N-Terminal Amino Acid Sequence and Amino Acid Sequence of Inner Peptide of Purified Enzyme The purified enzyme obtained in step (2) is subjected to SDS-polyacrylamide gel electrophoresis directly or after trypsin digestion, thereby resolving polypeptides. The polypeptides on the gel are then electroblotted onto a PVDF membrane (Immobilon Psq; Millipore). The membrane is stained with Coomassie Brilliant Blue. The stained bands are excised and subjected to amino acid sequence analyses using Shimadzu PSQ-1 amino acid sequencer. The results are shown below.

a) N-Terminal amino acid sequence of the non-treated enzyme:
(molecular weight: about 60,000);
Xaa-Thr-Pro-His-Asn-Pro-Asp-Ala (SEQ ID NO:4)
wherein Xaa represents Met or deletion.

b) Partially trypsin-degraded product: (molecular weight: about 50,000);
Glu-Ile-Gly-Ser-Val-Gly-Lys-Met-Glu-Ile-Gly-Arg-Xaa-Ala-Asn-Asp-Leu-Arg-Asn-Arg (SEQ ID NO:5)
wherein Xaa represents an unidentified amino acid residue.

c) Partially trypsin-degraded product: (molecular weight: about 10,000);

Ala-Ser-Gly-Ala-Lys-Ala-Pro-Glu-Phe-Gln-Glu-Leu-Tyr-Asp-Phe-Glu-Ala-Ala-Xaa-Leu-Xaa-Leu (SEQ ID NO:6)

wherein Xaa represents an unidentified amino acid residue. (The parentheses show molecular weights of the fractionated peptides.)

(4) Preparation of Probe

Based on the amino acid sequence information obtained in step (3), synthetic DNAs are prepared as primers. PCR (polymerase chain reaction) is performed using the chromosomal DNA of strain TN-3 obtained in step (1) as a template together with these primers.

Specifically, 1 µl of the TN-3 chromosomal DNA, 10 µl of a 10× reaction buffer, 4 µl of 10 mM dNTP, 1 µl (corresponding to 100 pmol) of each of primers #1 and #2, and 1 µl of ExTaq (Takara Shuzo Co., Ltd.) are mixed together to give a total volume of 100 µl. This solution is incubated sequentially at 95° C. for 30 seconds (denaturation step), at 55° C. for 30 seconds (annealing step) and at 72° C. for 2 minutes (elongation step) per cycle for 30 cycles. After the completion of the reaction, the reaction mixture is subjected to chloroform extraction (3 times) then ethanol precipitation, thereby recovering the amplified DNA. This DNA is separated by 1.0% agarose gel electrophoresis to obtain a DNA fragment of about 300 bp which is believed to encode the EDDSase of strain TN-3. The thus-obtained DNA fragment is labeled with DIG DNA Labeling Kit (Boehringer Mannheim) to prepare a probe.

(5) Preparation of DNA Library

To 10 µl of the TN-3 chromosomal DNA are added 5 µl of 10× restriction enzyme reaction buffer, 33 µl of sterilized water and 2 µl of restriction enzyme KpnI, and the mixture is allowed to react at 37° C. for 16 hours. Thereafter, DNA fragments are recovered by ethanol precipitation and electrophoresed on agarose gel. DNA fragments with sizes ranging from 6.5 kb to 5.5 kb are excised from the gel, recovered with DNA PREP (DIA IATRON), and inserted into the KpnI site of *E.coli* vector pUC18 using a ligation kit (Takara Shuzo Co., Ltd.) to prepare a recombinant DNA library.

The pUC18 fragment used in the above ligation is prepared as follows. To 2 µl of a pUC18 stock solution are added 5 µl of 10× restriction enzyme reaction buffer, 40 µl of sterilized water and 3 µl of restriction enzyme KpnI, and the mixture is reacted at 37° C. for 2 hours. After phenol treatment and ethanol precipitation, the resultant DNA is dried and dissolved in 50 µl of sterilized water. To this solution 1 µl of alkaline phosphatase (Takara Shuzo Co., Ltd.), 10 µl of 10× reaction buffer and 39 µl of sterilized water are added, and the mixture is allowed to react at 65° C. followed by phenol treatment and ethanol precipitation. The resultant DNA fragment is dried and dissolved in sterilized water.

(6) Preparation of *E.coli* Transformant and Screening of Recombinant DNA

*E.coli* strain JM109 is inoculated into 1 ml of LB medium (1% bacto-tryptone, 0.5% bacto-yeast extract, 0.5% NaCl) and pre-cultured at 37° C. for 5 hours under aerobic conditions. One hundred milliliters of this culture is added to 40 ml of SOB medium (2% bacto-tryptone, 0.5% bacto-yeast extract, 10 mM NaCl, 2.5 mM KCl, 1 mM $MgSO_4$, 1 mM $MgCl_2$) and cultured at 18° C. for 20 hours. This culture is centrifuged to harvest cells. Then, 13 ml of cold TF solution (20 mM PIPES-KOH (pH 6.0), 200 mM KCl, 10 mM $CaCl_2$, 40 mM $MnCl_2$) is added to the cells, and the mixture is left at 0° C. for 10 minutes. After removal of the supernatant by centrifugation, the precipitated *E.coli* cells are suspended in 3.2 ml of cold TF solution, to which 0.22 ml of dimethyl sulfoxide is added, and the suspension is left at 0° C. for 10 minutes. To 200 µl of the thus-prepared competent cells, 10 µl of the recombinant plasmid-containing solution (DNA library) prepared in step (5) is added, and the resultant mixture is left at 0° C. for 30 minutes, subjected to heat shock at 42° C. for 30 seconds, and cooled at 0° C. for 2 minutes. One milliliter of SOC medium (20 mM glucose, 2% bacto-tryptone, 0.5% bacto-yeast extract, 10 mM NaCl, 2.5 mM KCl, 1 mM $MgSO_4$, 1 mM $MgCl_2$) is then added, and the cells are shake-cultured at 37° C. for 1 hour. This culture is seeded in 200 µl portions on LB agar media containing 100 µg/ml ampicillin and cultured at 37° C. The transformant colonies formed on the agar media are screened for transformants containing the EDDSase gene by colony hybridization. Specifically, the transformants formed on the agar are transferred onto a nylon membrane (BIODYNE A, Japan Pall) and lysed to fix on the membrane. The membrane is then treated with the probe (about 300 bp) prepared in step (4), and colonies containing the recombinant DNA of interest are selected using DIG Luminescent Detection Kit (Boehringer Mannheim).

(7) Preparation of Recombinant Plasmid

The transformant selected in step (6) is cultured in 100 ml of LB medium overnight at 37° C. The cells are harvested and washed with sterilized water. To the cells are added 5 ml of Solution I (2 mM glucose, 10 mM EDTA, 25 mM Tris-HCl (pH 8)) and 25 mg of lysozyme, and the resultant mixture is left at 0° C. for 30 minutes. After addition of 10 ml of Solution II (1 N NaOH, 5% SDS) the mixture is left at 0° C. for 5 minutes, to which 7.5 ml of Solution III (3 M sodium acetate (pH 4.8)) is added. The mixture is left at 0° C. for 30 minutes and centrifuged to obtain the supernatant, to which 50 ml of ethanol is added. Following removal of the supernatant by centrifugation, to the precipitate are added 5 ml of solution IV (10 mM sodium acetate, 50 mM Tris-HCl (pH 8)) and 2.5 µl of ribonuclease solution A (10 mg/ml), and the mixture is left at room temperature for 20 minutes. Twelve ml of ethanol is added to recover the plasmid by centrifugation, which plasmid is then rinsed with 70% ethanol, dried and dissolved in 0.4 ml of sterilized water. The thus-obtained recombinant plasmid is named pEDS001.

(8) Restriction Mapping of pEDS001 and Identification of EDDSase Gene Region

Figure 2:
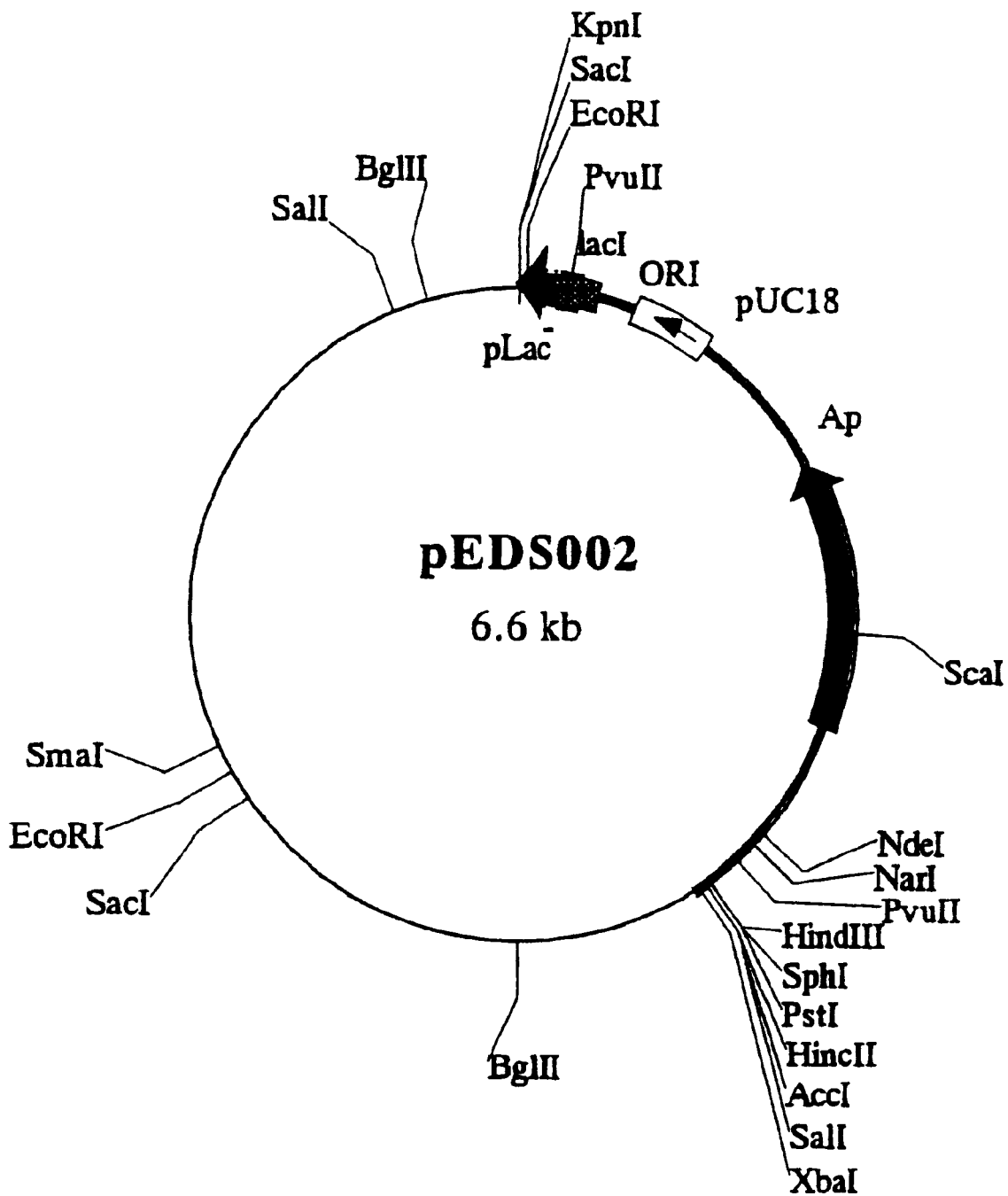
FIG. 2 is a restriction map of the plasmid pEDS002 in which an approximately 3.9 kb fragment cleaved from the plasmid pEDS001 with restriction enzymes KpnI and BamHI has been inserted into pUC18.
Figure 3:
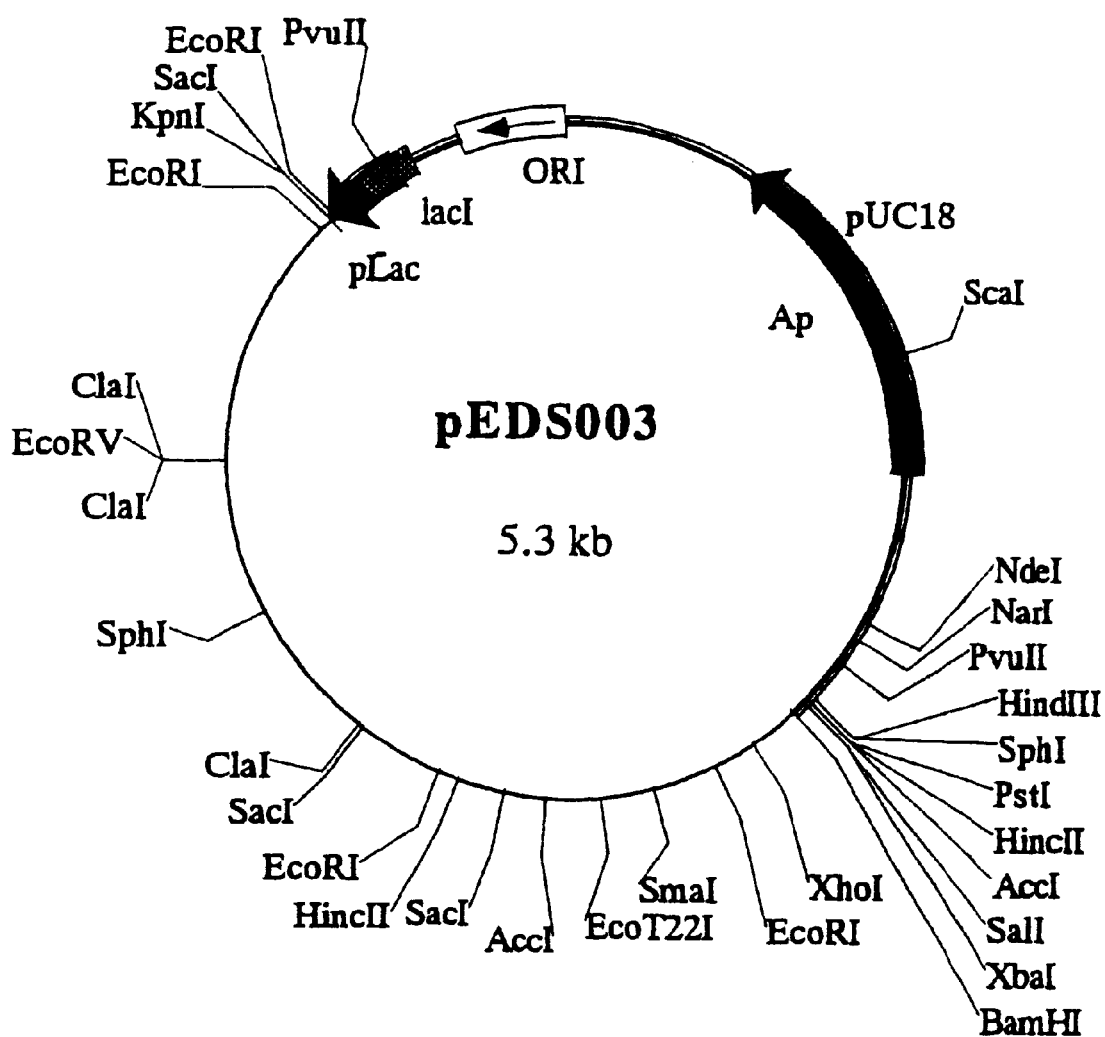
FIG. 3 is a restriction map of the plasmid pEDS003 in which an approximately 2.6 kb fragment cleaved from the plasmid pEDS001 with restriction enzymes KpnI and BamHI has been inserted into pUC18.
Figure 4:
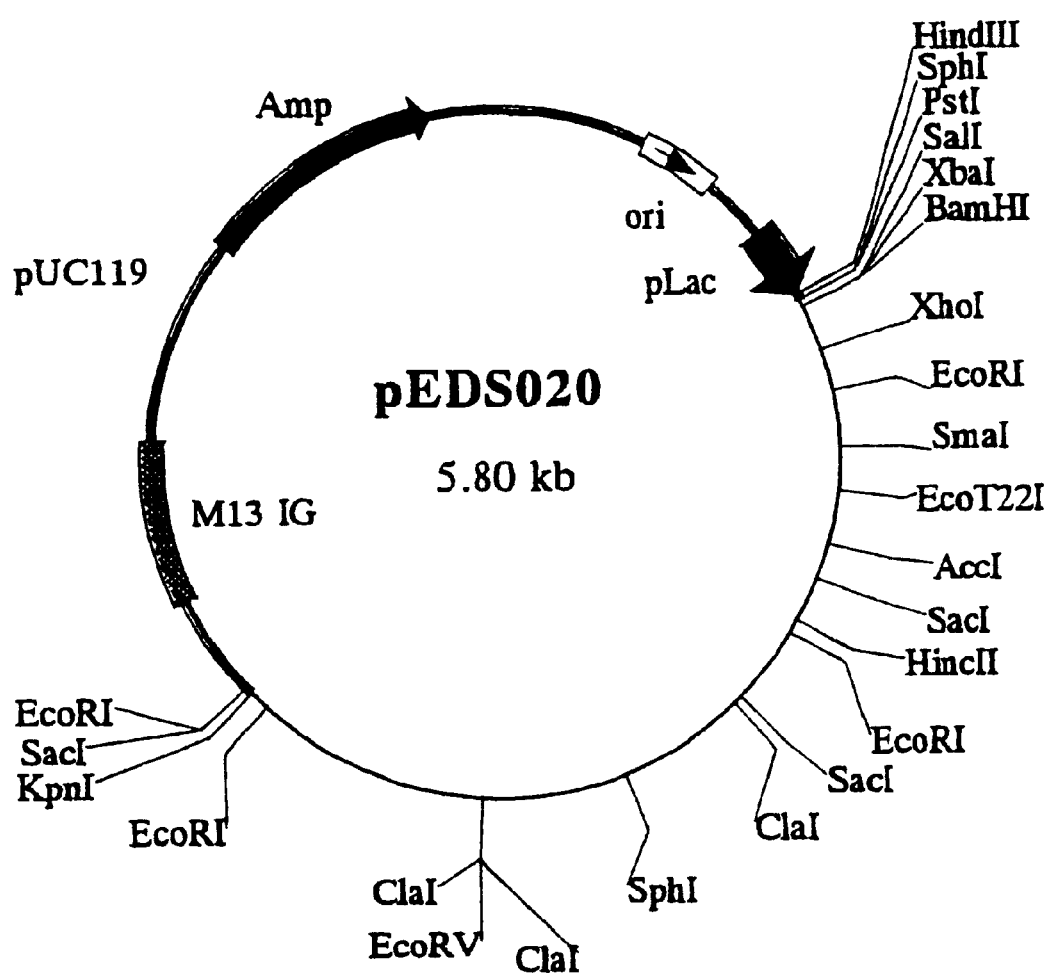
FIG. 4 is a restriction map of the plasmid pEDS020 in which an approximately 2.6 kb fragment cleaved from the plasmid pEDS003 with restriction enzymes KpnI and BamHI has been inserted into pUC119.

Plasmid pEDS001 obtained in step (7) is cleaved with several types of restriction enzymes to prepare a restriction map (FIG. 1). Furthermore, subcloning is conducted in a conventional manner. Specifically, pEDS001 is cleaved with restriction enzymes KpnI and BamHI. The resultant fragments are ligated to pUC18 which has been cleaved with the same restriction enzymes. *E.coli* strain JM109 is transformed with the obtained plasmid DNAs to yield a plasmid having an approximately 3.9 kb insert (pEDS002) (FIG. 2) and a plasmid having an approximately 2.6 kb insert (pEDS003) (FIG. 3). Each of these plasmids is cleaved with restriction enzymes BamHI, EcoRI, SacI, SacII, etc. and subjected to agarose gel electrophoresis. A fragment with which the probes hybridize is identified by Southern hybridization.

(9) Determination of DNA Sequence

DNA sequences around the region identified in step (8) are determined using a Pharmacia fluorescent sequencer, ALFII. As a result, the DNA sequence of SEQ ID NO:2 is obtained, and the open reading frame coding for the amino acid sequence of SEQ ID NO:1 is found therein. The search according to the amino acid sequence database NBRF (National Biomedical Research Foundation) reveals that this gene has 20–30% homology to the gene for delta-crystallin or argininosuccinate lyase. Both of these enzymes are known to have an activity of catalyzing condensation or decomposition reaction of fumaric acid and an amine (amino acid). The DNA sequence of the open reading frame is shown in SEQ ID NO:3.

(10) Preparation of Plasmid pEDS020 and *E.coli* Transformant, and EDDSase Activity of the Transformant To 2 μl of the recombinant plasmid pEDS003 obtained in step (8) which contains the EDDSase gene, 2 μl of 10× restriction enzyme reaction buffer, 15 μl of sterilized water and 1 μl of restriction enzyme KpnI are added, and the mixture is reacted at 37° C. for 2 hours. The plasmid is recovered by ethanol precipitation and dried. Then, 17 μl of sterilized water, 2 μl of 10× restriction enzyme reaction buffer and 1 μl of restriction enzyme BamHI are added, followed by 2-hour reaction at 37° C. From the reaction mixture, an approximately 2.6 kb fragment is separated by agarose gel electrophoresis and inserted into *E.coli* vector pUC119. Using this ligation solution, *E.coli* strain JM109 is transformed to yield a plasmid of interest. The thus-prepared plasmid and the transformant are named pEDS020 and JM109/PEDS020, respectively.

The transformant JM109/pEDS020 is inoculated into 1 ml of LB medium containing 50 mg/l of ampicillin and shake-cultured at 37° C. for 8 hours. Then, the total amount of cells are cultured in 40 ml of LB medium (containing 50 mg/l of ampicillin and 1 mM isopropyl-β-galactoside) at 37° C. for 30 hours. The resultant culture is washed with 10 mM sodium phosphate buffer (pH 8) and then suspended in 2 ml of the same buffer. An aliquot of the resultant cell suspension is suspended in 50 ml of an aqueous solution (pH 8) containing 342 mM fumaric acid and 171 mM ethylenediamine, and the suspension is reacted for 24 hours. After removal of the cells from the reaction mixture by centrifugation, ethylenediamine-N,N'-disuccinic acid is analyzed by HPLC (WAKOSIL 5C8, Wako Pure Chemical Industries) (using, as an eluent, 50 mM phosphoric acid solution, pH 2, containing 10 mM tetra-n-butylammonium hydroxide and 0.4 mM $CuSO_4$). According to the analysis, production of 50 mM (S,S)-ethylenediamine-N,N'-disuccinic acid is confirmed.

(11) Preparation of Plasmid pSE001

Figure 5:
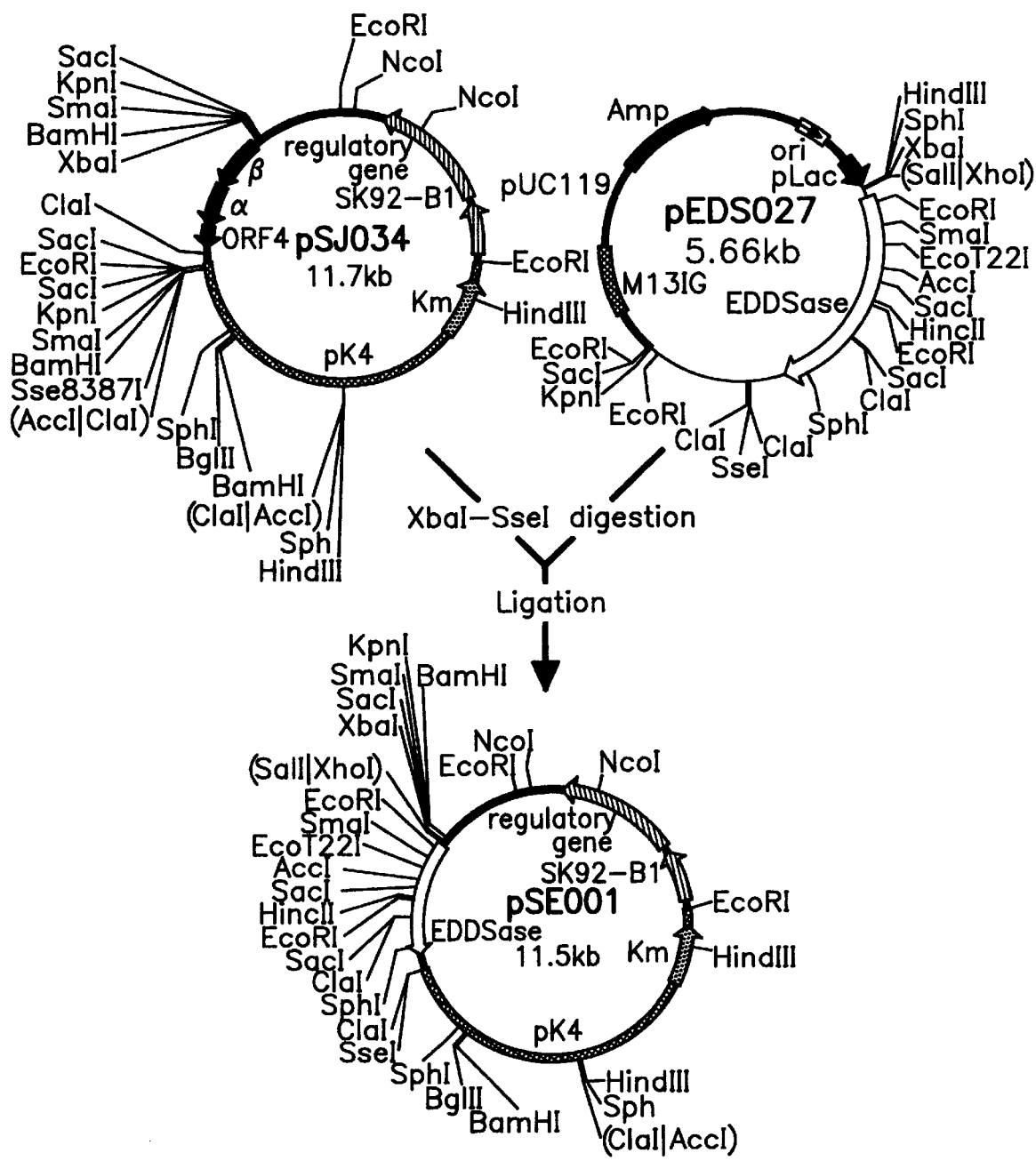
FIG. 5 shows construction of the plasmid pSE001.
Figure 6:
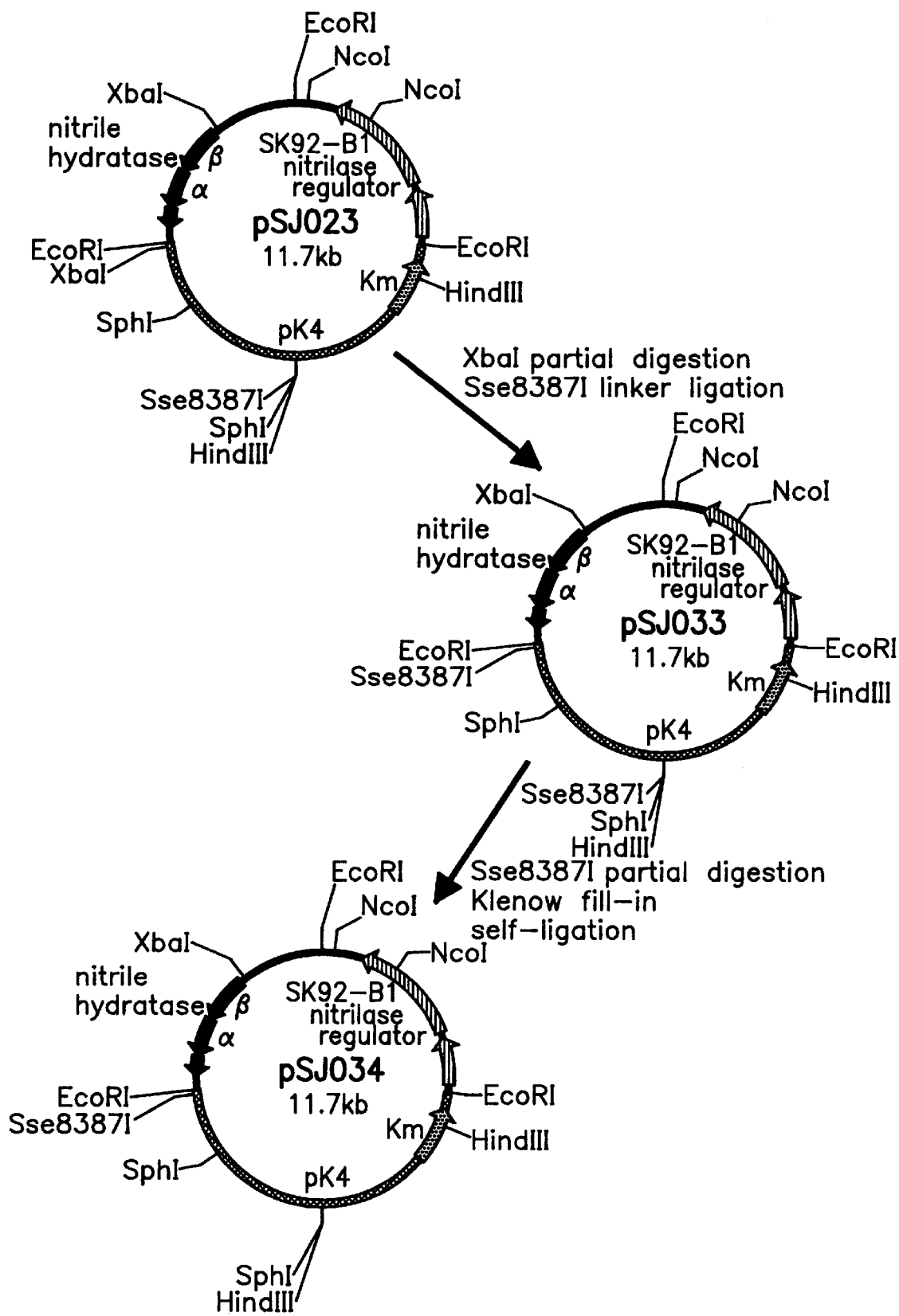
FIG. 6 shows construction of the plasmid pSJ034.

To 2 μl of plasmid pEDS020 obtained in Step (10), 2 μl of 10× restriction enzyme reaction buffer, 15 μl of sterilized water, 1 μl of restriction enzyme XhoI are added, and the mixture is reacted at 37° C. for 2 hours. The plasmid is recovered by ethanol precipitation and dried, to which 15 μl of sterilized water, 2 μl of a 10× klenow fragment buffer, 2 μl of a 10 mM dNTP's solution and 1 μl of a klenow fragment are added, followed by 2-hour reaction at 37° C. The DNA fragment is recovered by ethanol precipitation and dried, to which are added 8 μl of sterilized water, 1 μl of XbaI linker solution, and 16 μl of Solution A and 4 μl of Solution B both from Ligation kit (Takara Shuzo Co., Ltd.). The mixture is reacted at 16° C. for 4 hours. After transformation into JM109, a plasmid is obtained from the transformant, the plasmid having a change of the XhoI site of pEDS020 to XbaI site. To 2 μl of the obtained plasmid are added 2 μl of 10× restriction enzyme reaction buffer, 15 μl of sterilized water and 1 μl of restriction enzyme EcoRV, and the mixture is reacted at 37° C. for 2 hours. The DNA fragment is recovered by ethanol precipitation and dried. Then, 8 μl of sterilized water, 1 μl of Sse8387I linker solution, and 16 μl of Solution A and 4 μl of Solution B both from Ligation kit (Takara Shuzo Co., Ltd.) are added to the dried DNA, and the mixture is reacted at 16° C. for 4 hours and transformed into JM109. From the transformant, the plasmid pEDS027 is obtained which has a change of generally EcoRV site to Sse8387I site. To 2 μl of the thus-obtained plasmid are added 2 μl of 10× restriction enzyme reaction buffer, 14 μl of sterilized water, 1 μl of restriction enzyme XbaI and 1 μl of Sse83871, and the mixture is reacted at 37° C. for 2 hours. A 1.7 Kb band is separated from the reaction mixuture by agarose gel electrophoresis, which is then inserted into the XbaI-Sse83871 site of plasmid pSJ034 having a strong Rhodococcus promoter activity, thereby producing the transformant plasmid pSE001 (FIG. 5). The plasmid pSJ034 is prepared from the plasmid pSJ023 (Japanese Patent Application No. 9-65618) by the procedure shown in FIG. 6. The plasmid pSJ023 was deposited with the National Institute of Bioscience and Human-Technology, Agency of Industrial Science and Technology, MITI (Japan) as transformant *Rhodococcus rhodochrous* ATCC12674/pSJ023 (FERM P-16108) on Mar. 4, 1997 which was subsequently transferred to the international deposition as FERM BP-6232 on Jan. 21, 1998.

(12) Transformation of the Genus Rhodococcus Bacterium and EDDSase Activity of the Transformant The cultured *Rhodococcus rhodochorous* strain ATCC17895 is harvested in a logarithmic growth phase by centrifugation, washed with ice-cold sterilized water for 3 times, and suspended in sterilized water. One microliter of plasmid pSE001 and 10 μl of the cell suspension are mixed together and then ice-cooled. The suspension of the DNA and the cell is put into a cuvette, which is then subjected to an electric pulse treatment on Gene Pulser (BIO RAD) at 2.0 kV and 2000 HMS. The thus-treated solution is left in ice for 10 minutes and then subjected to heat shock at 37° C. for 10 minutes. Five-hundred milliliters of MYK medium (0.5% polypepton, 0.3% bacto-yeast extract, 0.3% bacto-malt extract, 0.2% $K_2HPO_4$ and 0.2% $KH_2PO_4$) is added to the solution and left at 30° C. for 5 hours. The resultant is streaked on MYK agar medium containing 50 mg/l kanamycin, which is then cultured at 30° C. for 3 days. The obtained transformant is named ATCC17895/pSE001.

The thus-prepared transformant is inoculated into 10 ml of MYK medium (containing 50 mg/l kanamycin), which is subjected to shake culture at 30° C. for 72 hours. One milliliter of the resultant is inoculated into 100 ml of a medium containing 1.5% glucose, 1% sodium glutamate, 0.1% bacto-yeast extract, 0.05% $KH_2PO_4$, 0.05% $K_2HPO_4$, 0.05% magnesium sulfate and 50 mg/l kanamycin (pH 7.2), and the mixture is then cultured at 30° C. for 60 hours. The obtained cell is used to conduct the reaction and analysis as described in step (10). As a result, production of 36 mM of (S,S)-ethylenediamine-N,N'-disuccinic acid is confirmed.

The reaction for producing an optically active aminopolycarboxylic acid represented by formula [1] is carried out by bringing either cells of any of the strains described above or a processed product thereof (e.g., debris of the strain cells, extracts of the strain cells, crude or purified enzymes from the strain cells, immobilized strain cells or enzymes, and strain cells or enzymes treated with an agent such as stabilizing agent) into contact with a mixture of fumaric acid and an amino group containing compound represented by formula [2] in water or a buffer solution, e.g., a phosphate buffer, carbonate buffer or borate buffer.

In general, the reaction is conducted at a temperature of from 0 to 50° C., preferably from 5 to 35° C., and a pH of from 5 to 11, preferably from 6 to 10. Although the concentrations of fumaric acid and the amino group containing compound represented by formula [2] vary depending on the reaction temperature and pH used, they each may be in the range of from 0.1% to the saturation concentration. The amount of the microorganism or processed product thereof used is generally from 0.01 to 5.0% by dry weight based on the amount of the substrates. The reaction may be conducted either batch wise or continuously.

For isolating the produced aminopolycarboxylic acid from the reaction mixture after completion of the reaction, known techniques such as removal of microorganisms, concentration, chromatography (e.g., HPLC), and crystallization may be used.

The procedures for producing aminopolycarboxylic acids can be carried out in similar manners to those described in JP-A-9-140390 or U.S. Pat. No. 5,707,836 whose entire contents are incorporated herein.

Hereinafter, the present invention will be described in detail by non-limiting Examples.

EXAMPLE 1

(1) Cultivation

Pseudomonas sp. strain TN-131, Paracoccus sp. strain TNO-5, Sphingomonas sp. strain TN-28 and Brevundimonas sp. strains TN-30 and TN-3 each were taken in the amount of one platinum loop from their slant media, inoculated into the medium set forth below, and subjected to shake culture at 30° C. for 4 days under aerobic conditions.

| Composition of the medium (pH 7.5, 100 ml) | |
|---|---|
| Ethylenediamine-N,N'-disuccinic acid | 0.2 g |
| Glucose | 0.2 g |
| Yeast extract | 0.1 g |
| Polypepton | 0.05 g |
| Magnesium sulfate (7 H$_2$O) | 0.1 g |
| Sodium sulfate | 0.28 g |
| Phosphate buffer | 25 mM |
| Solution of mixed metal salts* | 0.5 ml |

*This solution (100 ml) contained magnesium chloride.6H$_2$O (8 g), calcium chloride (0.8 g), manganese sulfate.4H$_2$O (0.6 g), ferric chloride.6H$_2$O (0.12 g) and zinc sulfate (0.06 g).

(2) Treatment for Removal of Fumarase Activity

The cultures of the strains were separately put in centrifuge tubes and centrifuged at 10,000 rpm at 5° C. for 15 minutes to collect the cultured strains which were then washed twice with 50 mM borate buffer (pH 9.2), diluted with the same buffer to give a concentration of 5 mg dry cell/ml, and treated in a water bath at 45° C. for 6 hours in order to remove the fumarase activity. After 2 hours, sampling was carried out.

(3) Assays for EDDSase and Fumarase Activities

The strains that had been subjected to the above-described treatment for removal of fumarase activity were assayed for their EDDSase and fumarase activities. Remaining activities of the enzymes were determined relative to each 100% activity of the untreated microorganisms.

EDDSase activity was assayed by reacting each strain in the reaction solution which contained 684 mM fumaric acid, 342 mM ethylene diamine and 342 mM magnesium hydroxide and had a pH adjusted to 8.5 with 6N NaOH, at a 1/10 cell concentration of the treated liquid at 30° C. for 1 day; and quantifying an amount of the formed (S,S)-ethylenediamine-N,N'-disuccinic acid (S,S-EDDS) by the method set forth below.

Fumarase activity was assayed by reacting each strain in the reaction solution containing 68.4 mM sodium L-malate and 50 M borate buffer and having a pH adjusted to 8.5 with 6N NaOH, at a 1/10 cell concentration of the treated liquid at 30° C. for 1 day; and quantifying an amount of the formed fumaric acid by the method set forth below.

Quantitation of Reaction Products

The S,S-EDDS, fumaric acid and L-malic acid were quantitatively analyzed by liquid chromatography after removing insoluble materials contained in the reaction mixtures by centrifugation at 15,000 rpm at 5° C. or 5 minutes. WAKOSIL 5C8 (Wako Pure Chemical Industries) was used as a quantitation column (eluate: 50 mM phosphate (pH 2) containing 10 h tetra-n-butylammonium hydroxide and 0.4 mM CuSO$_4$), and MCI GEL CRS 10W (produced by Mitsubishi Chemical Corporation) as an optical resolution column (eluate: 10 nM CuSO$_4$) respectively.

(4) Results

TABLE 1

| Strain | Treatment Time (hrs) | Remaining Activity (%) EDDSase (A) | Fumarase (B) | Ratio of Remaining Activities [−] (B/A) |
|---|---|---|---|---|
| TN-131 | 2 | 204 | 87 | 0.43 |
| | 6 | 234 | 23 | 0.1 |
| TNO-5 | 2 | 141 | <5 | <0.04 |
| | 6 | 214 | <5 | <0.03 |
| TN-28 | 2 | 459 | 114 | 0.25 |
| | 6 | 484 | 25 | 0.05 |
| TN-30 | 2 | 1030 | 180 | 0.17 |
| | 6 | 1100 | 52 | 0.05 |
| TN-3 | 2 | 101 | 70 | 0.69 |
| | 6 | 107 | 23 | 0.21 |

EXAMPLE 2

(1) Cultivation of Transformants

E.coli JM109/pEDS020

One plantinum loop of E.coli JM109/pEDS020 was taken from the slant medium, inoculated into LB medium (1% bacto-tryptone 0.5% bacto-yeast extract, 0.5% NaCl) containing 50 mg/l amipicillin, and subjected to shake culture at 37° C. for 8 hours. 2.5% (in volume) of the culture was inoculated into LB medium (containing 50 mg/l of ampicillin and 1 mM isopropyl-β-galactoside) and subjected to shake culture at 37° C. for 30 hours under aerobic conditions.

Rhocococcus rhodochrous ATCC17895/pSE001

One platinum loop of Rhocococcus rhodochrous ATCC17895/pSE001 was taken from the slant medium, inoculated into MYK medium (0.5% polypepton, 0.3% bacto-yeast extract, 0.3% bacto-malt extract, 0.2% K$_2$HPO$_4$, 0.2% KH$_2$PO$_4$) containing 50 mg/l of kanamycin, and subjected to shake culture at 30° C. for 72 hours. One percent (in volume) of the culture was inoculated into GGY medium (1.5% glucose, 1% sodium glutamate, 0.1% bacto-yeast extract, 0.05% K$_2$HPO$_4$, 0.05% KH$_2$PO$_4$, 0.05% magnesium sulfate, 50 mg/l kanamycin, pH 7.2) and subjected to shake culture at 30° C. for 60 hours under aerobic conditions.

(2) Treatment for Removal of Fumarase Activity
Fumarase activity was removed in the same manner as in Example 1.
(3) Assays for EDDSase and Fumarase Activities
EDDSase and fumarase activities were assayed in the same manner as in Example 1.
(4) Results

TABLE 2

| Strain | Treatment Time (hrs) | Remaining Activity (%) EDDSase (A) | Remaining Activity (%) Fumarase (B) | Ratio of Remaining Activities [-] (B/A) |
| --- | --- | --- | --- | --- |
| JM109/pED 020 | 2 | 104 | <5 | <0.05 |
|  | 6 | 106 | <5 | <0.05 |
| ATCC17895/ pSE001 | 2 | 244 | 219 | 0.9 |
|  | 6 | 411 | 53 | 0.13 |

EXAMPLE 3

(1) Cultivation of Transformant
E.coli JM109/pEDS020 was cultured in the same manner as in Example 2.
(2) Glutaraldehyde Treatment and Treatment for Removal of Fumarase Activity
The culture was put in a centrifuge tube and centrifuged at 10,000 rpm at 5° C. for 15 minutes to collect the transformant. After washed twice with 50 mM borate buffer (pH 9.2), the transformant was treated in the same buffer containing 1 mM (final concentration) glutaraldehyde at a final concentration of 5 mg dry cell/ml at 4° C. for 2 hours, washed twice with 100 mM borate buffer (pH 9.2), and diluted with the same buffer to a concentration of 5 mg dry cell/ml. This glutaraldehyde-treated transformant was subjected to treatment for removal of fumarase activity in a water bath at 45° C. for 6 hours. The untreated transformant diluted to the same concentration was employed as control.
(3) Assay for EDDSase and Fumarase Activities
EDDSase and fumarase activities were assayed in the same manner as in Example 1.
(4) Results

TABLE 3

| Glutaraldehyde Treatment | Remaining Activity (%) EDDSase (A) | Remaining Activity (%) Fumarase (B) | Ratio of Remaining Activities [-] (B/A) |
| --- | --- | --- | --- |
| No | 104 | <5 | <0.05 |
| Yes | 96 | <5 | <0.06 |

EXAMPLE 4

(1) Cultivation of Transformant
The transformant E.coli JM109/pEDS020 was cultured in the same manner as in Example 3.
(2) Treatment for Removal of Fumarase Activity
The culture was put in a centrifuge tube and centrifuged at 10,000 rpm at 5° C. for 15 minutes to collect the transformant. The transformant was then washed twice with 50 mM borate buffers which have been adjusted to pH values indicated in Table 4 with 6N NaOH or 5N sulfuric acid, diluted with the same respective buffers to a concentration of 5 mg dry cell/ml, and subjected to treatment for removal of fumarase activity in a water bath at 45° C. for 2 hours.
(3) Assay for EDDSase and Fumarase Activities
EDDSase and fumarase activities were assayed in the same manner as in Example 1.
(4) Results

TABLE 4

| pH | Remaining Activity (%) EDDSase (A) | Remaining Activity (%) Fumarase (B) | Ratio of Remaining Activities [-] (B/A) |
| --- | --- | --- | --- |
| 7.0 (Comparative Example) | 2 | 23 | 10 |
| 8.0 | 19 | 18 | 0.95 |
| 8.5 | 64 | <5 | <0.08 |
| 9.0 | 99 | <5 | <0.06 |
| 9.5 | 95 | <5 | <0.06 |
| 10.0 | 60 | <5 | <0.09 |
| 10.5 | 19 | <5 | <0.27 |

EXAMPLE 5

(1) Cultivation of Transformant
The transformant E.coli JM109/pEDS020 was cultured in the same manner as in Example 3.
(2) Treatment for Removal of Fumarase Activity
The culture was put in a centrifuge tube and centrifuged at 10,000 rpm at 5° C. for 15 minutes to collect the transformant which was then washed twice with salt solutions indicated in Table 5 (each having a pH adjusted to 9.2 with 6N NaOH or 5N sulfuric acid), diluted with the same salt solutions to a concentration of 5 mg dry cell/ml, and subjected to treatment for removal of fumarase activity in a water bath at 45° C. for 2 hours.
(3) Assay for EDDSase and Fumarase Activities
EDDSase and fumarase activities were assayed in the same manner as in Example 1.
(4) Results

TABLE 5

| Salts | Remaining Activity (%) EDDSase (A) | Remaining Activity (%) Fumarase (B) | Ratio of Remaining Activities [-] (B/A) |
| --- | --- | --- | --- |
| No additive (Comparative Example) | 1 | 45 | 45 |
| 5 mM sodium borate | 50 | 30 | 0.6 |
| 10 mM sodium borate | 83 | 20 | <0.25 |
| 50 mM sodium borate | 97 | <5 | <0.06 |
| 100 mM sodium borate | 104 | 12 | 0.12 |
| 500 mM sodium borate | 113 | 13 | 0.9 |
| 50 mM sodium phosphate | 98 | 10 | 0.1 |
| 50 mM ethylenediamine sulfate | 112 | <5 | <0.05 |
| 50 mM HEPES sulfate* | 94 | 7 | 0.07 |
| 10 mM sodium borate + 40 mM NaCl | 105 | 19 | 0.18 |
| 50 mM sodium borate + 50 mM ethylenediamine sulfate | 115 | <5 | 0.04 |

TABLE 5-continued

| Salts | Remaining Activity (%) | | Ratio of Remaining Activities |
|---|---|---|---|
| | EDDSase (A) | Fumarase (B) | [-] (B/A) |
| 50 mM sodium borate + 50 mM sodium fumarate | 115 | 17 | 0.15 |
| 50 mM sodium borate + 50 mM S,S-EDDS Na | 114 | 35 | 0.31 |
| 100 mM triethanolamine sulfate | 105 | 6 | 0.06 |
| 100 mM triethanolamine sulfate + 100 mM ethylenediamine sulfate | 101 | <5 | <0.05 |

*HEPES: N-2-hydroxyethylpiperazine-N'-2-ethanesulfonic acid

EXAMPLE 6

(1) Cultivation of Transformant

The transformant E.coli JM109/pEDS020 was cultured in the same manner as in Example 3.

(2) Treatment for removal of Fumarase Activity

The culture was put in a centrifuge tube and centrifuged at 10,000 rpm at 50° C. for 15 minutes to collect the transformant which was then washed twice with 100 mM borate buffer (pH 9.2), diluted with the same buffer to a concentration of 5 mg dry cell/ml, and subjected to treatment for removal of fumarase activity in a water bath at the temperatures for the period of times, both indicated in Table 6.

(3) Assay for EDDSase and Fumarase Activities

EDDSase and fumarase activities were assayed in the same manner as in Example 1.

(4) Results

TABLE 6

| Treatment Temperature (° C.) | Treatment Time (hrs) | Remaining Activity (%) | | Ratio of Remaining Activities |
|---|---|---|---|---|
| | | EDDSase (A) | Fumarase (B) | [-] (B/A) |
| 55 | 1/60 | 77 | 17 | 0.22 |
| 50 | 1/6 | 96 | 15 | 0.16 |
| | 1/2 | 45 | 12 | 0.27 |
| 45 | 2 | 104 | 15 | 0.14 |
| | 4 | 105 | <5 | <0.05 |
| | 24 | 68 | <5 | <0.08 |
| 40 | 24 | 94 | <5 | <0.06 |
| 30 | 48 | 98 | 8 | 0.08 |
| 20 | 168 | 112 | 26 | 0.23 |
| 4 | 336 | 118 | 7 | 0.06 |

EXAMPLE 7

(1) Cultivation of Transformant

The transformant E.coli JM109/pEDS020 was cultured in the same manner as in Example 3.

(2) Treatment for Removal of Fumarase Activity

The culture was put in a centrifuge tube and centrifuged at 10,000 rpm at 5° C. for 15 minutes to collect the transformant which was then washed twice with 100 mM borate buffer (pH 9.2), diluted with the same buffer to a concentration of 5 mg dry cell/ml, and subjected to treatment for removal of fumarase activity in a water bath at 45° C. for 4 hours.

(2) Reaction

The reaction was performed at 30° C. for 20 days using the reaction solution which contained 1232 mM fumaric acid, 616 mM ethylendiamine, 924 mM magnesium hydroxide and 20 mg dry cell/ml of the above-described treated or untreated transformant and had a pH adjusted to 8.5 with 6N NaOH. The pH was maintained at 8.5 with 6N NaOH.

The amounts of S,S-EDDS and L-malic acid in the reaction mixture were quantitated by the method described in Example 1.

(4) Results

| Treatment for Removal of Fumarase Activity | Production of S,S-EDDS (mM) | Production of Malic Acid (mM) |
|---|---|---|
| No (Comparative Example) | 387 | 315 |
| Yes | 553 | 3 |

As seen from the results described in the above Examples, the present invention provides a microbial catalyst in which fumarase activity can selectively be removed without lowering EDDSase activity, and which is usable for production of optically active aminopolycarboxyl acids with less fumaric acid loss.

Even when the EDDSase activity of a microorganism or processed product thereof is lost to some extent due to an alkaline treatment, the microorganism or processed product thereof can be used advantageously as a catalyst for producing optically active aminopolycarboxyl acids with less fumaric acid loss, as long as the proportion of the removed fumarase activity is relatively greater than the loss of the EDDSase activity.

Various other modifications will be apparent to and can be readily made by those skilled in the art without departing from the scope and spirit of this invention. Accordingly, it is not intended that the scope of the claims appended hereto be limited to the description as set forth herein, but rather that the claims be broadly construed.

What is claimed is:

1. A method for removing fumarase activity from a microorganism or processed product thereof having ethylenediamine-N,N'-disuccinic acid ethylenediamine lyase (EDDSase) activity, which comprises treating the microorganism or processed product thereof with an aqueous alkaline solution at a pH of 8.5 to 10.5 in the presence of at least one salt of an inorganic or organic acid other than aspartic acid having a concentration of 10 mM to 1000 mM.

2. A method according to claim 1, wherein the salt is selected from the group consisting of sodium, potassium, ammonium and amine salts of boric acid, phosphoric acid, hydrochloric acid, sulfuric acid, acetic acid, oxalic acid, fumaric acid, maleic acid and ethylenediamine-N,N'-disuccinic acid, and mixtures thereof.

3. A method according to claim 1, wherein the microorganism or processed product thereof is selected from the group consisting of bacteria belonging to the genera Pseudomonas, Paracoccus, Sphingomonas and Brevundimonas, and transformants in which a DNA encoding EDDSase has been introduced into a host bacterium that belongs to the genus Escherichia or Rhodococcus; or processed products thereof.

4. A method according to claim 1, wherein the microorganism or processed product thereof is selected from the group consisting to Pseudomonas sp. strain TN-131 (FERN BP-5418), Paracoccus sp. strain TNO-5 (FERM BP-6547), Sphingomonas sp. strain TN-28 (FERM BP-5419), Brevundimonas sp. strain TN-30 (FERM BP-5417) and Brevundimonas sp. strain TN-3 (FERM BP-5886), and transformants derived from the hosts Escherichia coli strain JM109 (ATCC53323) and *Rhocococcus rhodochrous* ATCC17895; or processed products thereof.

5. A method according to claim 1, 3 or 4, wherein the processed product thereof is selected from the group consisting of debris of the microorganisms, extracts of the microorganisms, crude or purified enzymes from the microorganisms, immobilized microorganisms or enzymes, and microorganisms or enzymes treated with an agent.

6. A method according to claim 1, wherein the concentration of the salt is in the range of 10 mM to 500 mm.

7. A method according to claim 1 wherein the pH of the aqueous alkaline solution ranges from 8.5 to 10.

8. A method according to claim 1 wherein the pH of the aqueous alkaline solution ranges from 9 to 9.5.

9. A method according to claim 1, wherein the treatment is carried out at a temperature ranging from a freezing temperature to 55° C.

10. A method according to claim 1, wherein the treatment is carried out over a period of about 1 minute to about 1 month.

11. A method according to claim 1, wherein the salt is selected from the group consisting of salts of boric acid, phosphoric acid, hydrochloric acid, sulfuric acid, acetic acid, oxalic acid, fumaric acid, maleic acid and ethylenediamine-N,N'-disuccinic acid, and mixtures thereof.

\* \* \* \* \*